(12) United States Patent
Lin et al.

(10) Patent No.: US 6,514,903 B2
(45) Date of Patent: Feb. 4, 2003

(54) PROCESS FOR PREPARING A CATALYST

(75) Inventors: Manhua Lin, Maple Glen, PA (US); Michael William Linsen, North Wales, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/425,671

(22) Filed: Oct. 22, 1999

(65) Prior Publication Data

US 2001/0049336 A1 Dec. 6, 2001

Related U.S. Application Data

(62) Division of application No. 09/316,007, filed on May 21, 1999, now Pat. No. 6,180,825.
(60) Provisional application No. 60/086,211, filed on May 21, 1998.

(51) Int. Cl.⁷ .................... B01J 23/10; B01J 23/26; B01J 23/28; B01J 23/42; B01J 23/44
(52) U.S. Cl. .............. 502/311; 502/304; 502/312; 502/313; 502/315; 502/316; 502/319; 502/321; 502/325; 502/326; 502/333; 502/334; 502/335; 502/336; 502/337; 502/338; 502/339; 502/353; 502/354; 502/355; 502/308; 502/309; 502/322; 502/324; 502/327; 502/332; 502/349; 502/351; 502/350
(58) Field of Search .................. 502/305, 311, 502/312, 304, 308, 313, 309, 315, 316, 314, 319, 322, 321, 324, 325, 327, 326, 332, 333, 349, 334, 351, 335, 350, 336, 337, 338, 339, 353, 354, 355

(56) References Cited

U.S. PATENT DOCUMENTS

| | | | |
|---|---|---|---|
| 4,014,925 A | | 3/1977 | Ferlazzo et al. |
| 4,219,670 A | | 8/1980 | Okada et al. |
| 4,277,375 A | | 7/1981 | Decker et al. |
| 4,339,355 A | | 7/1982 | Decker et al. |
| 4,966,990 A | | 10/1990 | Otake et al. |
| 5,049,692 A | | 9/1991 | Hatano et al. |
| 5,206,201 A | * | 4/1993 | Kishimoto et al. .......... 502/206 |
| 5,231,214 A | | 7/1993 | Ushikubo et al. |
| 5,281,745 A | | 1/1994 | Ushikubo et al. |
| 5,364,824 A | * | 11/1994 | Andrews et al. ............ 502/209 |
| 5,364,825 A | * | 11/1994 | Neumann et al. ........... 502/311 |
| 5,380,933 A | * | 1/1995 | Ushikubo et al. ........... 562/549 |
| 5,405,818 A | * | 4/1995 | De Thomas et al. ........ 502/151 |
| 5,449,821 A | * | 9/1995 | Neumann et al. ........... 562/546 |
| 5,472,925 A | * | 12/1995 | Ushikubo et al. ........... 502/312 |
| 5,583,086 A | * | 12/1996 | Tenten et al. ................ 502/249 |

FOREIGN PATENT DOCUMENTS

| | | |
|---|---|---|
| EP | 0 010 902 | 10/1979 |
| EP | 0 603 836 | 6/1994 |
| JP | 3170445 | 11/1989 |
| JP | 2067236 | 8/1998 |

OTHER PUBLICATIONS

Abstract of Japanese Laid–Open patent appln. No. 10–128112A (May 19, 1998).
Abstract of Japanese Laid–Open patent appln. No. 07–315842A (Dec. 5, 1995).
Abstract of Japanese Laid–Open patent appln. No. 10–057813A (Mar. 3, 1998).
Abstract of Japanese Laid–Open patent appln. No. 07–232071A (Sep. 5, 1995).

* cited by examiner

*Primary Examiner*—Elizabeth D. Wood
(74) *Attorney, Agent, or Firm*—Alan Holler

(57) ABSTRACT

An improved catalyst including a compound of the formula (I)

$$A_a M_m N_n X_x O_o \qquad (I)$$

wherein $0.25 < a < 0.98$, $0.003 < m < 0.5$, $0.003 < n < 0.5$, $0.003 < x < 0.5$ and o is dependent on the oxidation state of the other elements, A is selected from the group consisting of Mo, W, Fe, Nb, Ta, Zr, Ru and mixtures thereof; M is selected from the group consisting of V, Ce, Cr and mixtures thereof; N is selected from the group consisting of Te, Bi, Sb, Se and mixtures thereof; and X is selected from the group consisting of Nb, Ta, W, Ti, Al, Zr, Cr, Mn Fe, Ru, Co, Rh, Ni, Pd, Pt, Sb, Bi, B, In, Ce and mixtures thereof; is prepared by the process comprising:

(A) admixing metal compounds, at least one of which is an oxygen containing compound, and at least one solvent to form a solution;

(B) removing the solvent from the solution to obtain a catalyst precursor; and (C) calcining the catlyst under an inert atmosphere, wherein the inert atmosphere is not flowing over the catalyst precursor, to form a catalyst including said compound of the formula (I).

8 Claims, 1 Drawing Sheet

PROCESS FOR PREPARING A CATALYST

This is a Divisional of Application Ser. No. 09/316,007 filed May 21, 1999 and now U.S. Pat. No. 6,180,825, which claims the benefit of Provisional application Ser. No. 60/086,211, filed May 21, 1998.

This invention relates to a process for preparing a catalyst. In particular, the invention relates to a process for preparing a catalyst which is efficient in converting alkanes to unsaturated aldehydes and carboxylic acids, a catalyst prepared from the process, and a process for preparing unsaturated aldehydes and carboxylic acids using the catalyst.

Unsaturated aldehydes and carboxylic acids are important commercial chemicals. Of particular importance is (meth)acrylic acid. The highly reactive double bond and acid function of (meth)acrylic acid makes it especially suitable as a monomer which may be polymerized alone or with other monomers to produce commercially important polymers. These unsaturated acids are also useful as a starting material for esterification to produce commercially important (meth) acrylate esters. Materials derived from (meth)acrylic acid or esters of (meth)acrylic acids are useful as plastic sheets and parts, paints and other coatings, adhesives, caulks, sealants, and detergents as well as other applications.

The production of unsaturated carboxylic acids by oxidation of an olefin is well known in the art. Acrylic acid, for instance, may be commercially manufactured by the gas phase oxidation of propylene. It is also known that unsaturated carboxylic acids may also be prepared by oxidation of alkanes. For instance, acrylic acid may be prepared by the oxidation of propane. Such a process is especially desirable because alkanes generally have a lower cost than olefins. For example, at the time of filing this application propylene costs approximately three times more than propane. A suitable process for the oxidation of alkanes to unsaturated aldehydes or carboxylic acids which is commercially viable has yet to be achieved.

One impediment for the production of a commercially viable process for the catalytic oxidation of an alkane to an unsaturated carboxylic acid is the identification of a catalyst having adequate conversion and suitable selectivity, thereby providing sufficient yield of the unsaturated carboxylic acid end-product. U.S. Pat. No. 5,380,933 discloses a method for preparing a catalyst useful in the gas phase oxidation of an alkane to an unsaturated carboxylic acid. In the disclosed method, a catalyst was prepared by combining ammonium metavanadate, telluric acid and ammonium paramolybdate to obtain a uniform aqueous solution. To this solution was added ammonium niobium oxalate to obtain a slurry. The water was removed from the slurry to obtain a solid catalyst precursor. The solid catalyst precursor was molded into a tablet, sieved to a desired particle size and then calcined at 600° C. under a nitrogen stream to obtain the desired catalyst.

The resulting catalyst was asserted to be effective to convert propane to acrylic acid. However, as shown herein, the present inventor was unable to reproduce the asserted results using the preparation method of the '933 patent. While not wishing to be bound by theory, it is believed that the poor performance of the prior art method of '933 results from compositional or phase segregation of the component elements of the catalyst, e.g., in the slurry between solid and liquid phases and during calcining between the gas and various solid phases. The present inventor has now discovered a process for preparing a catalyst for catalyzing an alkane into an unsaturated aldehyde or carboxylic acid wherein phase segregation is minimized and improvement in selectivity, conversion, and yield are achieved.

In one aspect of the present invention, there is provided a process for preparing a catalyst including: (A) admixing metal compounds, at least one of which is an oxygen containing compound, and at least one solvent to form a solution; (B) removing the solvent from the solution to obtain a catalyst precursor; and (C) calcining the catalyst precursor at a temperature from 350° C. to 850° C. under an inert atmosphere to form a catalyst having the formula

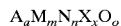

wherein 0.25<a<0.98, 0.003<m<0.5, 0.003<n<0.5, 0.003<x<0.5, and o is dependent on the oxidation state of the other elements, and A is selected from Mo, W, Fe, Nb, Ta, Zr, Ru, and mixtures thereof; M is selected from V, Ce, Cr, and mixtures thereof; N is selected from Te, Bi, Sb, Se, and mixtures thereof; and X is selected from Nb, Ta, W, Ti, Al, Zr, Cr, Mn, Fe, Ru, Co, Rh, Ni, Pd, Pt, Sb, Bi, B, In, Ce, and mixtures thereof.

In a second aspect of the present invention, there is provided a process for preparing a catalyst including: (A) admixing metal compounds, at least one of which is an oxygen containing compound, and water to form an aqueous solution; (B) removing the water from the aqueous solution to obtain a catalyst precursor; and (C) calcining the catalyst precursor at a temperature from 400° C. to 800° C. under an inert atmosphere, wherein the inert atmosphere is not flowing over the catalyst precursor, to form a catalyst having the formula

wherein 0.35<a<0.87, 0.045<m<0.37, 0.020<n<0.27, 0.005<x<0.35, and o is dependent on the oxidation state of the other elements, and A is selected from Mo, W, and mixtures thereof; M is selected from V, Ce, Cr, and mixtures thereof; N is selected from Te, Bi, Sb, and mixtures thereof; and X is selected from Nb, Ta, Zr, and mixtures thereof.

In a third aspect, the present invention provides a catalyst including a compound of the formula:

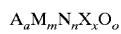

wherein 0.25<a<0.98, 0.003<m<0.5, 0.003<n<0.5, 0.003<x<0.5, and o is dependent on the oxidation state of the other elements, and A is selected from Mo, W, Fe, Nb, Ta, Zr, Ru, and mixtures thereof; M is selected from V, Ce, Cr, and mixtures thereof; N is selected from Te, Bi, Sb, Se, and mixtures thereof; and X is selected from Nb, Ta, W, Ti, Al, Zr, Cr, Mn, Fe, Ru, Co, Rh, Ni, Pd, Pt, Sb, Bi, B, In, Ce, and mixtures thereof; wherein said catalyst has a surface area of from 2 to 10 m²/g as determined by the BET method.

In additional aspects of the present invention, there is provided a catalyst prepared by the processes for preparing a catalyst of the present invention and processes for preparing unsaturated aldehydes or carboxylic acids including subjecting an alkane to catalytic oxidation in the presence of a catalyst prepared according to the process for preparing a catalyst of the present invention.

Figure 1:
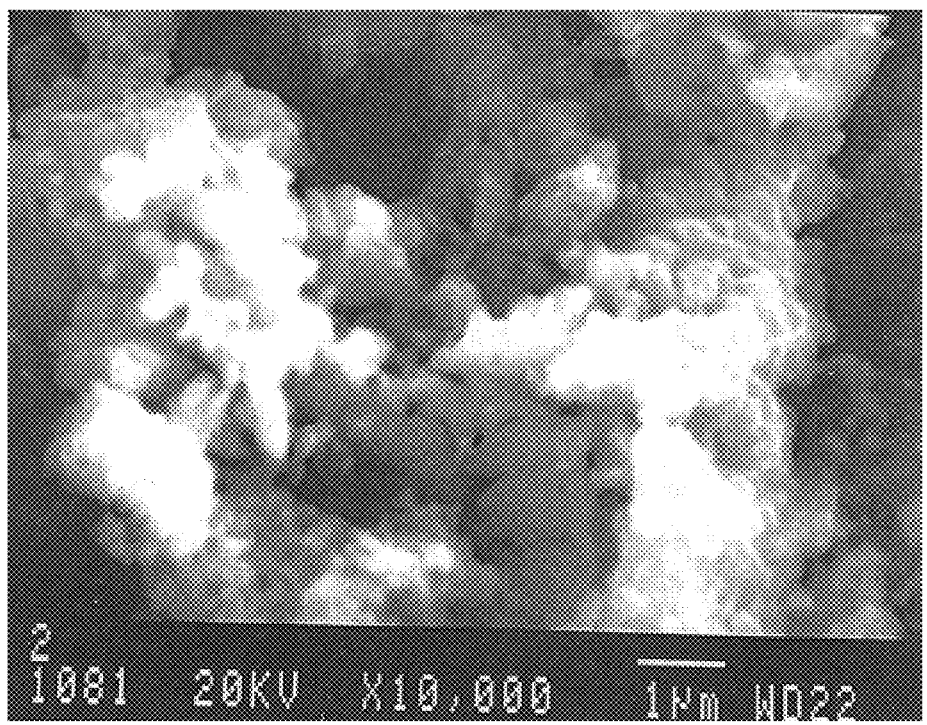
FIG. 1 depicts a scanning electron micrograph (SEM) of catalyst formed according to Example 1.

As used herein, the expression "(meth)acrylic acid" is intended to include both methacrylic acid and acrylic acid within its scope. In a like manner, the expression "(meth) acrylates" is intended to include both methacrylates and acrylates within its scope.

As used herein the terminology "($C_3$–$C_8$) alkane" means a straight chain or branched chain alkane having from 3 to 8 carbon atoms per alkane molecule.

As used herein the term "mixture" is meant to include within its scope includes all forms of mixtures including, but not limited to, simple mixtures as well as blends, alloys, etc.

For purposes of this application "% conversion" is equal to (moles of consumed alkane/moles of supplied alkane)× 100; "% selectivity" is equal to (moles of formed desired unsaturated carboxylic acid or aldehyde/moles of consumed alkane)×100; and "% yield" is equal to (moles of formed desired unsaturated carboxylic acid or aldehyde/moles of supplied alkane)×(carbon number of formed desired unsaturated carboxylic acid or aldehyde/carbon number of the supplied alkane)×100.

For purposes of this application by "solution" is meant that greater than 95 percent of metal solid added to a solvent is dissolved. It is to be understood that the greater the amount of metal solid not initially in solution, the poorer the performance of the catalyst derived therefrom will be.

As recited above, a process for preparing a catalyst is disclosed. In a first step of the process a solution is formed by admixing metal compounds, at least one of which contains oxygen, and at least one solvent in appropriate amounts to form the solution. Generally, the metal compounds contain elements A, M, N, X, and O. In one embodiment, A is selected from Mo, W, Fe, Nb, Ta, Zr, Ru and mixtures thereof; M is selected from V, Ce, Cr and mixtures thereof; N is selected from Te, Bi, Sb, Se and mixtures thereof; and X is selected from Nb, Ta, W, Ti, Al, Zr, Cr, Mn, Fe, Ru, Co, Rh, Ni, Pd, Pt, Sb, Bi, B, In, Ce and mixtures thereof. In a preferred embodiment, A is selected from Mo, W and mixtures thereof; M is selected from V, Ce, Cr and mixtures thereof; N is selected from Te, Bi, Sb and mixtures thereof; and X is selected from Nb, Ta, Zr, and mixtures thereof. In a more preferred embodiment, A is Mo, M is V, N is Te and X is Nb.

Suitable solvents include water, alcohols including, but not limited to, methanol, ethanol, propanol, and diols etc, as well as other polar solvents known in the art. Generally, water is preferred. The water is any water suitable for use in chemical synthesis including, without limitation, distilled water and deionized water. The amount of water present is that amount sufficient to keep the elements substantially in solution long enough to avoid or minimize compositional and/or phase segregation during the preparation steps. Accordingly, the amount of water will vary according to the amounts and solubility of materials combined. However, as stated above the amount of water must be sufficient to insure an aqueous solution is formed and not a slurry at the time of mixing.

Once the aqueous solution is formed, the water is removed by any suitable method known in the art to form a catalyst precursor. Such methods include, without limitation, vacuum drying, freeze drying, spray drying, rotary evaporation, and air drying. Vacuum drying is generally performed at pressures ranging from 10 to 500 mm/Hg. Freeze drying typically entails freezing the solution, using for instance liquid nitrogen, and drying the frozen solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and a pressure of from 10 mm/Hg to 760 mm/Hg, preferably at a bath temperature of from 40° C. to 90° C. and a pressure from 10 mm/Hg to 350 mm/Hg, more preferably from 40° C. to 60° C. and a pressure of from 10 mm/Hg to 40 mm/Hg. Air drying may be occur at temperatures ranging from 25° C. to 90° C. Rotary evaporation or air drying are generally preferred.

Once obtained, the catalyst precursor is calcined under an inert atmosphere. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen, more preferably argon. The inert atmosphere may flow over the surface of the catalyst precursor or may not flow (a static environment). It is important to understand that by non-flow atmosphere is meant that the inert gas is not allowed to flow over the surface of the catalyst precursor. It is preferred that the inert atmosphere not flow over the surface of the catalyst precursor. However, when the inert atmosphere does flow over the surface of the catalyst precursor, the flow rate can vary over a wide range, for example, at a space velocity from 1 to 500 $hr^{-1}$.

The calcination is typically done at a temperature of from 350° C. to 850° C., preferably from 400° C. to 700° C., more preferably from 500° C. to 640° C. The calcination is typically performed for an amount of time suitable to form the catalyst. In one embodiment, the calcination is performed from 0.5 to 30 hours, preferably from 1 to 25 hours and more preferably from 1 to 15 hours.

With calcination a catalyst is formed having the formula $$A_aM_mN_nX_xO_o$$

wherein A, M, N, and X are as described above. Molar ratios, a, m, n, and x are typically, from $0.25<a<0.98$, $0.003<m<0.5$, $0.003<n<0.5$, and $0.003<x<0.5$; preferably $0.35<a<0.87$, $0.045<m<0.37$, $0.020<n<0.27$, and $0.005<x<0.35$.

The molar ratio, o i.e., the amount of oxygen (O) present, is dependent on the oxidation state of the other elements in the catalyst. However, typically o is from 3 to 4.7, based on the other elements present in the catalyst.

Another aspect of the present invention is a catalyst for manufacturing an unsaturated aldehyde or a carboxylic acid from an alkane prepared by the process of the present invention. The catalyst is prepared as described above. The catalyst may be used as a solid catalyst alone or may be utilized with a suitable support such as, without limitation, silica, alumina, titania, aluminosilicate, diatomaceous earth, or zirconia. The shape of the catalyst can be any suitable shape and will depend upon the particular application of the catalyst. In a like manner, the particle size of the catalyst may be any suitable particle size depending on the particular use of the catalyst.

A further aspect of the present invention is a process for preparing an unsaturated aldehyde and a carboxylic acid including subjecting an alkane to catalytic oxidation in the presence of a catalyst prepared according to the present invention.

The starting materials are generally an alkane gas or gases and an at least one oxygen containing gas. It is preferred that the starting materials also include steam. Accordingly, a starting material gas is supplied to the system which includes a gas mixture of at least one alkane and steam. The at least one oxygen-containing gas may be included in this mixture or be supplied separately. Furthermore, a diluting gas such as an inert gas including, without limitation, nitrogen, argon, helium, steam, or carbon dioxide may also be included. The diluting gas may be used to dilute the starting material and/or to adjust the space velocity, the oxygen partial pressure, and the steam partial pressure.

Suitable molar ratios of the alkane/oxygen/diluting gas/water in the starting material gas mixture are known in the art as well as the feed ratio of alkane/air/steam. For instance suitable ranges are disclosed in U.S. Pat. No. 5,380,933.

The starting material alkane is generally any alkane suitable for gas phase oxidation into an unsaturated aldehyde or carboxylic acid. Generally, the alkane is a $C_3$–$C_8$ alkane, preferably propane, isobutane or n-butane, more preferably propane or isobutane, most preferably propane. Furthermore, in another embodiment the alkane may be a mixture of alkanes including $C_3$–$C_8$ alkanes as well as lower alkanes such as methane and ethane.

The at least one oxygen-containing gas used may be pure oxygen gas, an oxygen containing gas such as air, an oxygen enriched gas, or a mixture thereof.

In a preferred embodiment, the starting material is a gas mixture of propane, air, and steam. The starting gas mixture is subjected to catalytic oxidation in the presence of the catalyst of the present invention. The catalyst may be in a fluidized bed or a fixed bed reactor. The reaction is generally conducted under atmospheric pressure, but may be conducted under elevated or reduced pressure. The reaction temperature is generally from 200° C. to 550° C., preferably 300° C. to 480° C., more preferably 350° C. to 440° C. The gas space velocity is generally 100 to 10,000 $hr^{-1}$, preferably 300 to 6,000 $hr^{-1}$, more preferably 300 to 3,000 $hr^{-1}$.

Also, in the method of the present invention it is to be understood that an unsaturated aldehyde may also be formed. For instance when propane is the starting alkane, acrolein may be formed and when isobutane is the starting alkane, methacrolein may be formed.

Abbreviations used throughout this application are:
° C.=degrees Centigrade
mm=millimeters
Hg=Mercury
g=grams
cm=centimeters
mmole=millimoles
%=percent by weight
ml/min=milliliters per minute
$N_2$=nitrogen The following examples illustrate the process of the present invention. Based on the amount of starting material used, if there was no compositional segregation, or there was no loss of certain elements during the preparation steps, all of the catalyst samples prepared as follows should have an empirical formula of $Mo_1V_{0.3}Te_{0.23}Nb_{0.10-0.12}O_n$ where n is determined by the oxidation state of the other elements. The solutions or slurries containing the desired metal elements were prepared by heating the appropriate compounds in water at a temperature ranging from 25° C. to 95° C. When necessary, the solutions or slurries were cooled to temperatures ranging from 25° C. to 60° C. The water was then removed from the solutions or slurries by the appropriate drying method at pressures ranging from 760 mm/Hg to 10 mm/Hg.

EXAMPLE 1

Catalyst Precursor Solution Dried By Rotary Evaporation And Calcined Under Argon, Non-Flow Atmosphere In a flask containing 420 g of water, 25.7 g of ammonium heptamolybdate tetrahydrate (Aldrich Chemical Company), 5.1 g of ammonium metavanadate (Aldrich Chemical Company) and 7.7 g of telluric acid (Aldrich Chemical Company) were dissolved upon heating to 80° C. After cooling to 39° C., 114.6 g of an aqueous solution of niobium oxalate (Reference Metals Company) containing 17.34 mmole of niobium was mixed to obtain a solution. The water of this solution was removed via a rotary evaporator with a warm water bath at 50° C. and 28 mm/Hg to obtain 44 g of precursor solid. Twenty g of the catalyst precursor solid was calcined in a covered crucible pre-purged with argon, non-flow environment at 600° C. for 2 hours. The oven had previously been heated to 200° C. and held for one hour, then ramped to 600° C. During the calcination, the covered crucible was in a covered beaker with an Ar space velocity of 57 $hr^{-1}$. Because of the covered crucible, the argon did not flow over the precursor surface, but rather served to insure that the atmosphere outside the crucible remained argon. The atmosphere inside the crucible remained argon and off gasses from the catalyst. The catalyst thus obtained was pressed in a mold and then broken and sieved to 10–20 mesh granules. Ten g of the granules were packed into a 1.1 cm inside diameter stainless steel U-tube reactor for gas phase propane oxidation. The oxidation was conducted with a reactor bath (molten salt) temperature of 390° C., a feed ratio of propane/air/steam of 1/15/14, and a space velocity of 1,200 $hr^{-1}$. The effluent from the reactor was condensed to separate the liquid phase (the condensable material) and the gas phase. The gas phase was analyzed by gas chromatography ("GC") to determine the propane conversion. The liquid phase was also analyzed by GC for the yield of acrylic acid. The results are shown in Table 1. The catalyst was also analyzed by x-ray diffraction to determine its crystalline structure. The results are shown in Table 5. The catalyst surface was also analyzed by scanning electron microscopy. The results are shown in FIG. 1. FIG. 1 shows that the catalyst formed according to Example 1 is very porous. The BET surface area was determined to be 5.23 $m^2/g$.

EXAMPLE 2

Catalyst Precursor Solution Dried By Rotary Evaporation And Calcined Under Nitroen, Non-Flow Atmosphere Forty-three grams of catalyst precursor was prepared in the same manner as Example 1. Twenty-one g of the catalyst precursor solid was calcined in a covered crucible pre-purged with nitrogen, non-flow environment at 600° C. for 2 hours. During the calcination, the crucible was placed in a covered beaker with a nitrogen space velocity of 57–283 $hr^{-1}$. The catalyst thus obtained was pressed in a mold and then broken and sieved to 10–20 mesh granules. Twelve g of the granules were packed into a 1.1 cm inside diameter stainless steel U-tube reactor for gas phase propane oxidation. The oxidation was conducted with a reactor bath temperature of 390° C., a feed ratio of propane/air/steam of 1/15/16, and a space velocity of 1,565 $hr^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1.

EXAMPLE 3

Figure 2:
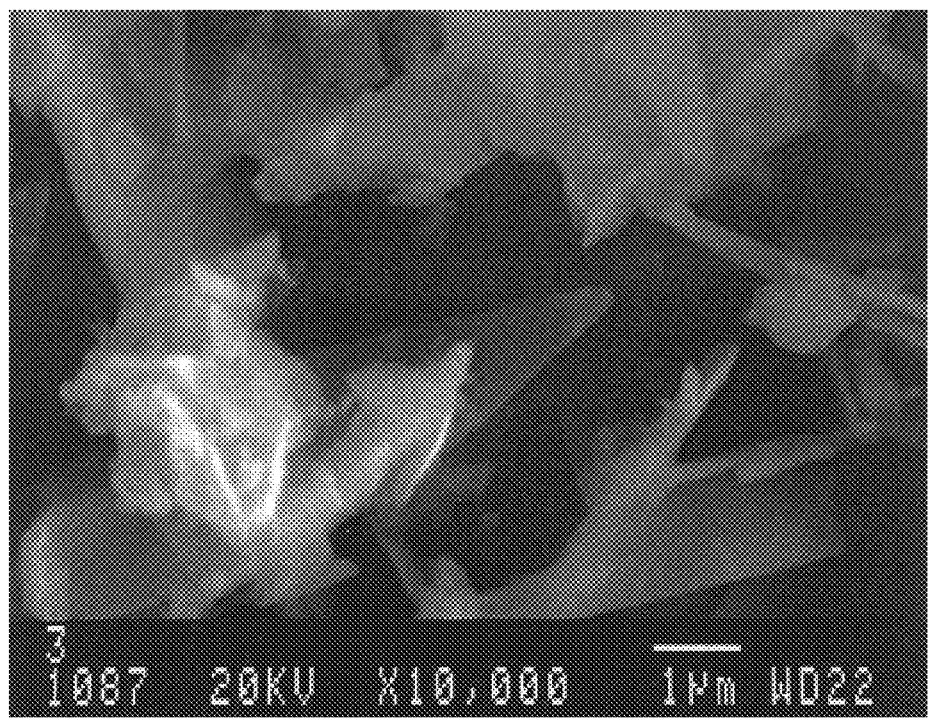
FIG. 2 shows that the catalyst calcined under air (Example 3) has larger crystals than the catalyst formed under argon. The catalyst calcined under air also has a smooth surface and is less porous than the catalyst formed under argon.

Catalyst Precursor Solution Dried By Rotary Evaporation And Calcined Under Air, Flow Atmosphere Twenty g of catalyst precursor solid from Example 1 was calcined under air at 600° C. for 2 hours. The catalyst thus obtained was pressed in a mold and then broken and sieved to 10–20 mesh granules. Ten g of the granules were packed into a 1.1 cm inside diameter stainless steel U-tube reactor for gas phase propane oxidation. The oxidation was conducted with a reactor bath temperature of 390° C., a feed ratio of propane/air/steam of 1/15/13, and a space velocity of 1,200 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1. The catalyst was also analyzed by x-ray diffraction to determine its crystalline structure. The results are shown in Table 5. The catalyst surface was also analyzed by scanning electron microscopy. The results are shown in FIG. 2. The BET surface area was determined to be 0.87 m$^2$/g.

EXAMPLE 4

Catalyst Precursor Solution Air Dried And Calcined Under Argon, Non-Flow Atmosphere Following the same procedure as Example 1, a solution containing Mo, V, Te and Nb was prepared. The solution was poured into a container with a large flat bottom. The solution gelled and dried slowly under atmospheric pressure and ambient temperature. A catalyst precursor solid was obtained and calcined in the same manner as Example 1. Eleven g of the granules thus obtained were packed into a 1.1 cm inside diameter stainless steel U-tube reactor for gas phase propane oxidation. The oxidation was conducted with a reactor bath temperature of 391° C., a feed ratio of propane/air/steam of 1/15/14, and a space velocity of 1,200 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1.

EXAMPLE 5

Catalyst Precursor Slurry Dried By Rotary Evaporation And Calcined Under Argon, Non-Flow Atmosphere In a flask containing 650 g of water, 158 g of ammonium heptamolybdate tetrahydrate, 31.4 g of ammonium metavanadate and 47.2 g of telluric acid were dissolved upon heating to 85° C. After cooling to a 45° C. solution, 814 g of an aqueous solution of niobium oxalate containing 111 mmole of niobium was added to the solution, resulting in 1,750 g of a slurry. One-quarter of the slurry was placed in a rotary evaporator with a warm water bath to remove water (as in Example 1), which resulted in 67 g of catalyst precursor solid. Twenty-six g of the precursor solid was calcined in an inert, non-flow environment at 600° C. for 2 hours (as in Example 1). The catalyst thus obtained was pressed in a mold and then broken and sieved to 10–20 mesh granules. Some of the granules (12.8 g) were packed into a 1.1 cm inside diameter stainless steel U-tube reactor for gas phase propane oxidation. The oxidation was conducted at a 389° C. reactor bath temperature, a feed ratio of propane/air/steam of 1/15/16, and a space velocity of 1,286 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1. The catalyst and catalyst precursor were analyzed by Inductively Coupled Plasma Atomic Emission Spectrometry ("ICP-AES") for Te, Mo, V, and Nb content. The results are shown in Tables 2 and 3. The catalyst was also analyzed by x-ray diffraction to determine its crystalline structure. The results are shown in Table 5.

EXAMPLE 6

Catalyst Precursor Slurry Dried By Rotary Evaporation And Calcined Under Nitrogen, Flow Atmosphere Twenty-five g of the same catalyst precursor solid of Example 5 was calcined in a quartz calcination flask with a nitrogen space velocity of 780 hr$^{-1}$ at 600° C. for 2 hours. The catalyst thus obtained was pressed in a mold and then broken and sieved to 10–20 mesh granules. Fourteen g of the granules were packed into a cm inside diameter stainless steel U-tube reactor for gas phase propane oxidation. The oxidation was conducted at a 389° C. reactor bath temperature, a feed ratio of propane/air/steam of 1/15/15, and a space velocity of 1,241 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1. The catalyst was analyzed for Te content by ICP-AES. The results are shown in Table 2.

EXAMPLE 7

Catalyst Precursor Slurry Dried By Freeze Drying And Calcined Under Argon, Non-Flow Atmosphere Two hundred ninety g of the slurry prepared in Example 5 was frozen drop by drop in a liquid nitrogen bath, then vacuum dried to obtain 43 g of powder solid. Twenty-seven g of the catalyst precursor solid was pressed in a mold and then broken and sieved to 10–20 mesh granules, then calcined in an argon, non-flow environment at 600° C. for 2 hours. The catalyst thus obtained was sieved to 10–20 mesh again to obtain a granule sample. Fifteen g of the granules were packed into a 1.1 cm inside diameter stainless steel U-tube reactor for gas phase propane oxidation. The oxidation was conducted at a 389° C. reactor bath temperature, a feed ratio of propane/air/steam of 1/15/16, and a space velocity of 1,286 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1. The catalyst was also analyzed by x-ray diffraction to determine its crystalline structure. The results are shown in Table 5.

EXAMPLE 8

Catalyst From The Precipitate Of The Slurry, Precipitate Dried By Air And Calcined Under Argon, Non-Flow Atmosphere Five hundred seventy five g of the slurry from Example 5 was filtered through a fine filter paper to separate the solid from the mother liquor. The solid was dried under atmospheric pressure at ambient temperature, resulting in 24 g of catalyst precursor. The catalyst precursor was calcined and prepared in the same manner as Example 1. Twelve g of the granules were packed into a 1.1 cm inside diameter stainless steel U-tube reactor for gas phase propane oxidation. The oxidation was conducted at a 390° C. reactor bath temperature, a feed ratio of propane/air/steam of 1/15/17, and a space velocity of 1,333 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1. The catalyst precursor was analyzed by ICP-AES for relative metal content. The results are shown in Table 3. The catalyst was analyzed by x-ray diffraction to determine its crystalline structure. The results are shown in Table 5.

EXAMPLE 9

Catalyst From Mother Liquor of the Slurry, Mother Liquor Dried By Rotary Evaporation And Calcined Under Argon, Non-Flow Atmosphere The mother liquor from Example 8 was dried by rotary evaporation in the same manner as Example 1, resulting in 62 g of solid catalyst precursor. Twenty g of the catalyst precursor was calcined and prepared in the same manner as Example 1. Thirteen g of the granules were packed into a 1.1 cm inside diameter stainless steel U-tube reactor for gas phase propane oxidation. The oxidation was conducted at a 390° C. reactor bath temperature, a feed ratio of propane/air/steam of 1/15/17, and a space velocity of 1,333 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1. The precursor was analyzed by ICP-AES for relative metal content. The results are shown in Table 3. The catalyst was also analyzed by x-ray diffraction to determine its crystalline structure. The results are shown in Table 5.

EXAMPLE 10

Precursor Solution Dried By Rotary Evaporation And Calcined Under Argon, Non-Flow Atmosphere Sixty-one grams of catalyst precursor was prepared in the same manner as Example 1. Twenty-five g of this solid was calcined under the same conditions as Example 1 to yield 17.7 g of solid. This solid was pressed in a mold and then broken and sieved to 10–20 mesh granules. Fourteen g of the granules were packed into a 1.1 cm inside diameter stainless steel U-tube reactor for gas phase propane oxidation. The oxidation was conducted with a reactor bath temperature of 390° C., a feed ratio of propane/air/steam of 1/15/13, and a space velocity of 1,161 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1. The catalyst was analyzed for Te content by ICP-AES. The results are shown in Table 2.

EXAMPLE 11

Catalyst Precursor Solution Dried By Rotary Evaporation And Calcined Under Argon, Flow Atmosphere Twenty-five g of catalyst precursor from Example 10 was calcined in a quartz calcination flask with an argon space velocity of 540 hr$^{-1}$ at 600° C. for 2 hours to yield 16.8 g of solid. The catalyst thus obtained was pressed in a mold and then broken and sieved to 10–20 mesh granules. Fourteen g of the granules were packed into a 1.1 cm inside diameter stainless steel U-tube reactor for gas phase propane oxidation. The oxidation was conducted with a reactor bath temperature of 390° C., a feed ratio of propane/air/steam of 1/16/16, and a space velocity of 1,241 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1. The catalyst was analyzed for Te content by ICP-AES. The results are shown in Table 2.

EXAMPLE 12

Catalyst Precursor Solution Dried By Rotary Evaporation And Calcined Under Argon, Non-Flow Atmosphere, With Post-Calcination Grinding Twenty grams of catalyst was prepared in the same manner as Example 1. This solid was ground to fine powder in a mortar and then dispersed with 66 g of water to obtain a slurry. The water in this slurry was removed via rotary evaporation to recover the solid which was then calcined again under the same conditions to yield 19.4 g of solid. This solid was pressed in a mold and then broken and sieved to 10–20 mesh granules. Thirteen g of the granules were packed into a 1.1 cm inside diameter stainless steel U-tube reactor for gas phase propane oxidation. The oxidation was conducted with a reactor bath temperature of 390° C., a feed ratio of propane/air/steam of 1/15/15.4, and a space velocity of 1,241 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 1.

TABLE 1

| Example | Pre-Drying | Drying | Calcination | conv. (%) | Sel. (%) | Yield (%) |
| --- | --- | --- | --- | --- | --- | --- |
| 1 | solution | rotavap | Ar non-flow | 69 | 55 | 38 |
| 2 | solution | rotavap | N$_2$ non-flow | 49 | 57 | 28 |
| 3 | solution | rotavap | air | 0 | — | 0 |
| 4 | solution | air | Ar non-flow | 49 | 53 | 26 |
| 5 | slurry | rotavap | Ar non-flow | 43 | 53 | 23 |
| 6 | slurry | rotavap | N$_2$ flow | 68 | 17 | 12 |
| 7 | slurry | freeze-dry | Ar non-flow | 19 | 49 | 9 |
| 8 | precipitate of slurry | air | Ar non-flow | 4 | 75 | 3 |
| 9 | mother liquid of slurry | rotavap | Ar non-flow | 3 | 33 | 1 |
| 10 | solution | rotavap | Ar non-flow | 59 | 48 | 28 |
| 11 | solution | rotavap | Ar flow | 57 | 23 | 13 |
| 12 | solution | rotavap | Ar non-flow | 71 | 59 | 42 | conv. (%) = percent of propane converted
sel. (%) = selectivity of propane conversion to acrylic acid in percent
yield (%) = the yield of acrylic acid in percent
rotavap = rotary evaporation

| Data Comparisons From Table 1 | | |
| --- | --- | --- |
| Comparison | Preparation Variables | Yield Ratio |
| Example 1/3 | inert non-flow/air | 38/0 = infinity |
| Example 1/5 | solution/slurry | 38/23 = 165% |
| Example 10/11 | non-flow/flow | 28/13 = 215% |
| Example 5/7 | rotavap/freeze-dry | 23/9 = 256% |

The data in Table 1 above indicate that a prepared catalyst is much more effective at converting propane to acrylic acid when calcined under an inert, non-flow atmosphere than when calcined under air (see Examples 1 and 3). Furthermore, the data indicate that a prepared catalyst is more effective at converting propane to acrylic acid when the catalyst is formed from a solution rather than a slurry (see Examples 1 and 5). The data of Table 1 also indicate that a prepared catalyst is more effective at converting propane to acrylic acid when the catalyst is calcined under a non-flow atmosphere rather than a flow atmosphere (see Examples 10 and 11). Finally, the data in Table 1 indicate that a prepared catalyst is more effective at converting propane to acrylic acid when the catalyst is initially dried by rotary evaporation rather than freeze drying (see Examples 5 and 7).

TABLE 2

| Example | Weight Percent Te In Catalyst |
| --- | --- |
| 5 | 13 |
| 6 | 9.8 (75 percent of theoretical) |
| $Mo_1V a_{0.3}Te_{0.23}Nb_{0.11}O_{4.5}$ | 13 |
| 10 | 13 |
| 11 | 10 |

The data in Table 2 show the loss of from 23 to 25 weight percent of the Te in the catalyst after calcination in a flow environment (see Examples 6 and 11), whereas in a non-flow environment (Examples 5 and 10) the weight percent of Te is comparable to the calculated theoretical value. This indicates that the catalyst is better formed in a non-flow environment. Particularly, loss of Te from the catalyst is shown when a flow environment is utilized during calcination. Accordingly, it is postulated that loss of substituent metal results in the lower yields shown in Table 1 for catalysts calcined in a flowing environment.

TABLE 3

| | Weight Percent Metal In Precursor | | | |
| --- | --- | --- | --- | --- |
| Example | Mo | V | Te | Nb |
| 5 | 43.3 | 6.9 | 11.3 | 4.0 |
| 8 | 36.8 | 5.2 | 12.2 | 13.4 |
| 9 | 46.1 | 7.5 | 11.1 | 0.3 |

The data in Table 3 demonstrate that the elements are not equally distributed between the aqueous phase and the solid phase of the slurry when the catalyst is prepared from a slurry. This results in the final catalyst having a compositional phase-segregation, therefore a less effective catalyst.

EXAMPLE 13

Catalyst Precursor Slurry Dried By Freeze Drying And Calcined Under Nitrogen, Flow Atmosphere In a flask containing 650 g of water, 158 g of ammonium heptamolybdate tetrahydrate, 31.4 g of ammonium metavanadate and 47.2 g of telluric acid were dissolved upon heating to 60° C. This solution was mixed with 360 g of an aqueous solution of niobium oxalate containing 111 mmole of niobium to form a slurry in a 50–60° C. water bath. Some of this slurry (831 g) was frozen in a liquid nitrogen bath then vacuum dried to obtain a catalyst powdery precursor solid. A portion of this catalyst precursor solid was pressed in a mold and then broken and sieved to 10–20 mesh granules, then calcined in a $N_2$ atmosphere, with a space velocity of 180–300 $hr^{-1}$ at 600° C. for 2 hours. The catalyst thus obtained was sieved to 10–20 mesh again to obtain a granule sample. Twenty g of the granules were packed into a 1.1 cm inside diameter stainless steel U-tube reactor for gas phase propane oxidation. The oxidation was conducted at a 385° C. reactor bath temperature, a feed ratio of propane/air/steam of 1/15/13, and a space velocity of 1,125 $hr^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 4. The catalyst was also analyzed by x-ray diffraction to determine its crystalline structure. The results are shown in Table 5.

EXAMPLE 14

Catalyst Precursor Slurry Dried By Heat Evaporation And Calcined Under Nitrogen, Flow Atmosphere Four hundred sixteen g of the slurry from Example 13 was stirred in an open beaker in the same water bath until dry to obtained a catalyst precursor solid. The catalyst precursor solid was pressed in a mold and then broken and sieved to 10–20 mesh granules, then calcined and prepared in the same manner as Example 10. The catalyst thus obtained was sieved to 10–20 mesh again to obtain a granule sample. Twenty-three g of the granules were packed into a 1.1 cm inside diameter stainless steel U-tube reactor for gas phase propane oxidation. The oxidation was conducted at a 391° C. reactor bath temperature, a feed ratio of propane/air/steam of 1/15/12, and a space velocity of 1,286 $hr^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 4. The catalyst was also analyzed by x-ray diffraction to determine its crystalline structure. The results are shown in Table 5.

EXAMPLE 15

Catalyst Precursor Slurry Dried By Spray Drying And Calcined Under Nitrogen, Flow Atmosphere In a flask containing 162 ml of water, 39.5 g of ammonium heptamolybdate tetrahydrate, 7.9 g of ammonium metavanadate and 11.8 g of telluric acid were dissolved upon heating to 80° C. This solution was mixed with 140 g of ammonium niobium oxalate (Advanced Materials Company) aqueous solution containing 53.6 mmole of niobium to form a slurry. This slurry was spray-dried in a small lab spray dryer with nitrogen as the carrier gas, an inlet temperature of 162° C., and an outlet temperature of 100–110° C. to result in a powdery catalyst precursor solid. A portion of this precursor solid was pressed in a mold, broken and sieved to 10–20 mesh granules, and then calcined in the same manner as Example 10 to obtain 22 g of granule catalyst. Twenty g of the granules were packed into a 1.1 cm inside diameter stainless steel U-tube reactor for gas phase propane oxidation. The oxidation was conducted at a 385° C. reactor bath temperature, a feed ratio of propane/air/steam of 1/15/14, and a space velocity of 1,161 $hr^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 4. The catalyst was also analyzed by x-ray diffraction to determine its crystalline structure. The results are shown in Table 5.

EXAMPLE 16

Catalyst Precursor Slurry Dried By Freeze Drying And Calcined Under Nitrogen, Flow Atmosphere A slurry was prepared in the same way as Example 15. This slurry was frozen in a liquid nitrogen bath drop by drop then vacuum dried to obtain a powdery catalyst precursor solid. A portion of this catalyst precursor solid was calcined in the same manner as Example 13 resulting in catalyst granules. Nineteen g of the granules were packed into a 1.1 cm inside diameter stainless steel U-tube reactor for gas phase propane oxidation. The oxidation was conducted at a 384° C. reactor bath temperature, a feed ratio of propane/air/steam of 1/15/12, and a space velocity of 1,440 hr$^{-1}$. The effluent from the reactor was condensed to separate the liquid phase and the gas phase. The gas phase was analyzed by GC to determine the propane conversion. The liquid phase was also analyzed by GC for the yield of acrylic acid. The results are shown in Table 4.

TABLE 4

| Example | pre-drying | drying | calcination | conv. (%) | sel. (%) | yield (%) |
|---|---|---|---|---|---|---|
| 13 | slurry | freeze-dry | N$_2$-flow | 13 | 25 | 3.3 |
| 14 | slurry | heat evaporation | N$_2$-flow | 1 | — | 0 |
| 15 | slurry | spray-dry | N$_2$-flow | 51 | 1.6 | 0.8 |
| 16 | slurry | freeze-dry | N$_2$-flow | 8 | 27 | 2.1 | conv. (%) = percent of propane converted
sel. (%) = selectivity of propane conversion to acrylic acid in percent
yield (%) = the yield of acrylic acid in percent

| | Comparisons With Data From Table 4 | |
|---|---|---|
| comparison | Preparation variables | yield ratio |
| Example 13/14 | freeze-dry/heat evaporation | 3.3/0 –> infinitive |
| Example 16/15 | freeze-dry/spray-dry | 2.1/0.8 = 263% |

TABLE 5

| Example | 22.1° | 28.2° | 36.2° | 45.2° | 50.0° |
|---|---|---|---|---|---|
| 1 | X | X | X | X | X |
| 3 | O | O | O | O | O |
| 5 | X | X | X | X | X |
| 7 | X | X | X | X | X |
| 8 | X | X | O | X | O |
| 9 | X | X | O | O | X |
| 13 | X | X | X | X | X |
| 14 | X | X | X | O | X |
| 15 | X | O | O | X | O |

X = peak present
O = peak not present

It is known that effective catalysts of this invention should have x-ray diffraction peaks at a diffraction angle of 2θ at 22.1°, 28.2°, 36.2°, 45.2°, and 50.0°. The data in Table 5 above indicates that an effective catalyst is not formed when calcined under air, dried via heat evaporation or spray drying, or originating from the precipitate phase or mother liquor phase of the slurry.

The above examples demonstrate that the process of this invention is more effective at converting propane to acrylic acid than any known process.

What is claimed:

1. An improved process for preparing a catalyst having the formula

wherein 0.25<a<0.98, 0.003<m<0.5, 0.003<n<0.5, 0.003<x<0.5 and o is dependent on the oxidation state of the other elements, and A is selected from the group consisting of Mo, W, Fe, Nb, Ta, Zr, Ru, and mixtures thereof, M is selected from group consisting of V, Ce, Cr, and mixtures thereof, N is selected from the group consisting of Te, Bi, Sb, Se, and mixtures thereof, and X is selected from the group consisting of Nb, Ta, W, Ti, Al, Zr, Cr, Mn, Fe, Ru, Co, Rh, Ni, Pd, Pt, Sb, Bi, B, In, Ce, and mixtures thereof, said process comprising:

admixing metal compounds, at least one of which is an oxygen containing compound, and at least one solvent to form a mixture, removing the solvent from the mixture to obtain a catalyst precursor, and calcining the catalyst precursor to form said catalyst; wherein the improvement comprises:

(A) admixing said metal compounds, at least one of which is an oxygen containing compound, and said at least one solvent to form a solution;

(B) removing the solvent from said solution, by the application of heat and vacuum pressure to said solution, to obtain a catalyst precursor; and (C) calcining said catalyst precursor at a temperature from 350° C. to 850° C. under an inert atmosphere, wherein said inert atmopshere is not flowing over said catalyst precursor, to from said catalyst having the formula

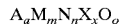

wherein 0.25<a<0.98, 0.003<m<0.5, 0.003<n<0.5, 0.003<x<0.5 and o is dependent on the oxidation state of the other elements, A is selected from the group consisting of Mo, W, Fe, Nb, Ta, Zr, Ru and mixtures thereof, M is selected from the group consisting of V, Ce, Cr and mixtures thereof, N is selected from the group consisting of T, Bi, Sb, Se and mixtures thereof, and X is selected from the group consisting of Nb, Ta, W, Ti, Al, Zr, Cr, Mn, Fe, Ru, Co, Rh, Ni, Pd, Pt, Bi, B, Ce. and mixtures thereof.

2. The process according to claim 1 wherein the catalyst comprises 0.35<a<0.87, 0.045<m<0.37, 0.020<n<0.27, and 0.005<x<0.35.

3. The process according to claim 1, wherein the catalyst is calcined at a temperature from 400° C. to 800° C.

4. The process according to claim 1, wherein A is selected from the group consisting of Mo, W and mixtures thereof; M is selected from the group consisting of V, Ce, Cr and mixtures thereof; N is selected from the group consisting of Te, Bi, Sb and mixtures thereof; and X is selected from the group consisting of Nb, Ta, Zr and mixtures thereof.

5. The process according to claim 1, wherein the inert atmosphere comprises at least one of argon and nitrogen.

6. An improved process for preparing a catalyst having the formula

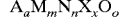

wherein 0.35<a<0.87, 0.045<m<0.37, 0.020<n<0.27, 0.005<x<0.35 and o is dependent on the oxidation state of the other elements, A is selected from the group consisting of Mo, W and mixtures thereof, M is selected from the group consisting of V, Ce, Cr and mixtures thereof, N is selected from the group consisting of Te, Bi, Sb and mixtures thereof, and X is selected from the group consisting of Nb, Ta, Zr and mixtures thereof, said process comprising:

admixing metal compounds, at least one of which is an oxygen containing compound, and water to form an aqueous mixture, removing the water from the aqueous mixture to obtain a catalyst precursor, and calcining the catalyst precursor to form said catalyst; wherein the improvement comprises:
(A) admixing said metal compounds, at least one of which is an oxygen containing compound, and said water to form an aqueous solution;
(B) removing the water from said aqueous solution, by the application of heat and vacuum pressure to said aqueous solution, to obtain a catalyst precursor; and
(C) calcining said catalyst precursor at a temperature from 400° C. to 800° C. under an inert atmosphere, wherein said inert atmosphere is not flowing over the catalyst precursor, to form said catalyst having the formula $$A_aM_mN_nX_xO_o$$

wherein $0.35<a<0.87$, $0.045<m<0.37$, $0.020<n<0.27$, $0.005<X<0.35$ and o is dependent on the oxidation state of the other elements, A is selected from the group consisting of Mo, W and mixtures thereof; M is selected from the group consisting of V, Ce, Cr and mixtures thereof; N is selected from the group consisting of Te, Bi, Sb and mixtures thereof; and X is selected from the group consisting of Nb, Ta, Zr and mixtures thereof.

7. An improved process for preparing a catalyst having the formula $$A_aM_mN_nX_xO_o$$

wherein $0.25<a<0.98$, $0.003<m<0.5$, $0.003<n<0.5$, $0.003<x<0.5$ and o is dependent on the oxidation state of the other elements, A is Mo, M is V, N is Te, and X is Nb, said process comprising:

admixing metal compounds, at least one of which is an oxygen containing compound, and at least one solvent to form a mixture, removing the solvent from the mixture to obtain a catalyst precursor, and calcining the catalyst precursor to form said catalyst; wherein the improvement comprises:

(A) admixing said metal compounds, at least one of which is an oxygen containing compound, and said at least one solvent to form a solution;

(B) removing the solvent from said solution to obtain a catalyst precursor; and (C) calcining said catalyst precursor at a temperature from 350° C. to 850° C. under an inert atmosphere, wherein said inert atmosphere is not flowing over said catalyst precursor, to form said catalyst having the formula $$A_aM_mN_nX_xO_o$$

wherein $0.25<a<0.98$, $0.003<m<0.5$, $0.003<n<0.5$, $0.003<x<0.5$ and o is dependent on the oxidation state of the other elements, A is Mo, M is V, N is Te, and X is Nb.

8. An improved process for preparing a catalyst having the formula $$A_aM_mN_nX_xO_o$$

wherein $0.35<a<0.87$, $0.045<m<0.37$, $0.020<n<0.27$, $0.005<x<0.35$ and o is dependent on the oxidation state of the other elements, A is Mo, M is V, N is Te, and X is Nb, said process comprising:

admixing metal compounds, at least one of which is an oxygen containing compound, and water to form an aqueous mixture, removing the water from the aqueous mixture to obtain a catalyst precursor, and calcining the catalyst precursor to form said catalyst; wherein the improvement comprises:

(A) admixing said metal compounds, at least one of which is an oxygen containing compound, and said water to form an aqueous solution;

(B) removing the water from said aqueous solution to obtain a catalyst precursor; and (C) calcining said catalyst precursor at a temperature from 400° C. to 800° C. under an inert atmosphere, wherein said inert atmosphere is not flowing over the catalyst precursor, to form said catalyst having the formula $$A_aM_mN_nX_xO_o$$

wherein $0.35<a<0.87$, $0.045<m<0.37$, $0.020<n<0.27$, $0.005<X<0.35$ and o is dependent on the oxidation state of the other elements, A is Mo, M is V, N is Te, and X is Nb.

* * * * *